(12) United States Patent
Liviero et al.

(10) Patent No.: US 6,521,669 B1
(45) Date of Patent: Feb. 18, 2003

(54) HYDROXYSTILBENE COMPOUNDS FOR REDUCING/INHIBITING PROTEIN GLYCATION

(75) Inventors: Christel Liviero, Paris (FR); Lionel Breton, Versailles (FR); Hervé Pageon, Montgeron (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/617,041

(22) Filed: Jul. 14, 2000

(30) Foreign Application Priority Data

Jul. 16, 1999 (FR) .............................. 99 09267

(51) Int. Cl.⁷ ..................... A61K 31/065; A61K 31/05; A61K 7/00; A61K 7/06
(52) U.S. Cl. ................. 514/726; 514/733; 514/734; 424/401; 424/70.1
(58) Field of Search ................ 514/726, 733, 514/734; 424/401, 70.1

(56) References Cited

U.S. PATENT DOCUMENTS 5,770,571 A * 6/1998 Cerami et al. ........... 424/130.1
6,124,364 A * 9/2000 Breton et al. ............... 514/733
6,147,121 A * 11/2000 Breton et al. ............... 514/726

FOREIGN PATENT DOCUMENTS

| FR | 2777186 | 10/1996 |
| FR | 2777183 | 10/1999 |
| FR | 2777184 | 10/1999 |
| WO | WO-99/04747 | * 2/1999 |

OTHER PUBLICATIONS

Patent Abstracts of Japan, vol. 013, No. 227 (C–600), May 25, 1989.
Patent Abstracts of Japan, vol. 1996, No. 11, Nov. 29, 1996.
Patent Abstracts of Japan, vol. 015, No. 297, Jul. 29, 1991.
Patent Abstracts of Japan, vol. 1998, No. 04, Mar. 31, 1998.
Patent Abstracts of Japan, vol. 1998, No. 06, Apr. 30, 1998.

* cited by examiner

*Primary Examiner*—Sreeni Padmanabhan
*Assistant Examiner*—Michael A. Willis
(74) *Attorney, Agent, or Firm*—Burns, Doane, Swecker & Mathis, L.L.P.

(57) ABSTRACT

The hydroxystilbenes are well suited for reducing or inhibiting the glycation of certain substrates, for example the proteins of nails and/or hair, advantageously to preventatively and/or curatively combat glycation-related aging of the nails/hair.

15 Claims, No Drawings

HYDROXYSTILBENE COMPOUNDS FOR REDUCING/INHIBITING PROTEIN GLYCATION

CROSS-REFERENCE TO PRIORITY APPLICATION

This application claims priority under 35 U.S.C. §119 of FR-99/09267, filed Jul. 16, 1999, hereby expressly incorporated by reference.

BACKGROUND OF THE INVENTION

1. Technical Field of the Invention

The present invention relates to the administration of at least one hydroxystilbene compound, or composition comprised thereof, to an individual subject in need of such treatment, to reduce or even inhibit the glycation of proteins, particularly the proteins of the skin and/or of the structures associated therewith.

2. Description of the Prior Art

Glycation is a non-enzymatic process involving a saccharide (glucose or ribose) which reacts according to the Maillard reaction with an amino group of an amino acid residue (for example such as lysine), particularly an amino acid residue of a protein, to form a Schiff's base. This Schiff's base, after undergoing an Amadori molecular rearrangement, can lead, by a series of reactions, to bridging, particularly intramolecular bridging such as, for example, of pentosidine type.

This phenomenon increases uniformly with age. It is characterized by the appearance of glycation products whose content increases uniformly as a function of age. The glycation products are, for example, pyrraline, carboxymethyllysine, pentosidine, crossline, $N^\epsilon$(2-carboxyethyl)lysine (CEL), glyoxallysine dimer (GOLD), methylglyoxallysine dimer (MOLD), 3DG-ARG imidazolone, versperlysines A, B and C, threosidine or the advanced glycosylation end products (or AGEs).

The glycation of proteins is thus a universal phenomenon, which is well known to occur in the skin, particularly in its dermal component, but which also occurs in the structures associated therewith such as the nails or the hair, particularly on keratins and more generally in any protein system provided that the conditions required for glycation are satisfied.

Human skin consists of two components, namely, a superficial component, the epidermis, and a deep component, the dermis.

Natural human skin is principally composed of three types of cell: the keratinocytes, which constitute the vast majority, the melanocytes and the Langerhans cells. Each of these cell types contributes, by virtue of its intrinsic functions, towards the essential role played in the body by the skin.

The dermis provides the epidermis with a solid support. It is also the nourishing factor of the epidermis. It consists principally of fibroblasts and of an extracellular matrix itself composed of different extracellular proteins, among which are, in particular, collagen fibers, elastin and various glycoproteins This assembly of extracellular components is synthesized by the fibroblasts. Leukocytes, mastocytes and tissue macrophages are also found in the dermis. Finally, the dermis contains blood vessels and nerve fibers.

Taking account of their activity in the synthesis of the extracellular matrix proteins (proteoglycans, collagen fibers and other structural glycoproteins), the fibroblasts are the principal factors involved in the structural development of the dermis.

The collagen fibers provide the dermis with solidity. They are very strong but are sensitive to certain enzymes generally known as collagenases. In the dermis, the collagen fibers consist of fibrils bonded together, thus forming more than ten different types of structure. The structure of the dermis is essentially due to the overlapping of the packed collagen fibers. The collagen fibers contribute in respect of the tonicity of the skin. The collagen fibers are regularly renewed, but this renewal decreases with age, thus promoting, especially, a thinning of the dermis. It is also accepted that extrinsic factors such as ultraviolet radiation, tobacco or certain treatments (retinoic acid and derivatives, glucocorticoids, vitamin D and derivatives, for example) also have an effect on the skin and on its collagen level.

As regards the dermal component of the skin, glycation intervenes mainly in the dermis, on the collagen fibers, according to the process described above. The glycation of collagen increases uniformly with age, resulting in a uniform increase in the content of glycation products in the skin.

Without wishing to be bound to any particular theory in respect of aging of the skin, it should be noted that other modifications of collagen which might also be a consequence of glycation, such as a reduction in heat-denaturation, an increase in the resistance to enzymatic digestion and an increase in intermolecular bridges, have been demonstrated in the course of aging of the skin (Tanaka S. et al., 1988, *J. Mol. Biol.*, 203, 495–505; Takahashi M. et al., 1995, *Analytical Biochemistry*, 232, 158–162). Furthermore, modifications due to the glycation of certain constituents of the basal membrane such as collagen IV, laminin and fibronectin have been demonstrated (Tarsio JF. et al., 1985, *Diabetes*, 34, 477–484; Tarsio JF. et al., 1988, *Diabetes*, 37, 532–539; Sternberg M. et al., 1995, C.R. *Soc. Biol.*, 189, 967–985).

Thus, it is understood that in the course of aging of the skin, the physicochemical properties of collagen modify and this collagen becomes more difficult to dissolve and degrade.

Thus, one of the components of aged skin clearly appears to be glycated collagen.

It is very well known to this art that the skin results from a close combination between at least two components of which it is composed, namely, the epidermis and the dermis. The interactions between the dermis and the epidermis are such that it is reasonable to expect that a modification of one may have consequences on the other. It may be suspected that aging of the dermis, in particular with its glycation phenomena will inevitably have consequences on the epidermis with which is associated. In the course of aging of the skin, the glycation of collagen should result in modifications of the epidermis which are necessarily implicated in aging of the epidermis.

Thus, if the glycation of dermal proteins, particularly collagen, elicits nothing more than harmful consequences on the skin, similar consequences are to be expected of the glycation of the proteins in the structures associated with the skin such as, for example, the nails and/or the hair and, indeed, of any protein system.

It will thus be appreciated that need continues to exist for active agents/species which reduce or even inhibit the phenomenon of glycation of proteins.

SUMMARY OF THE INVENTION

It has now surprisingly and unexpectedly been determined that the hydroxystilbenes elicit the effect of reducing or even inhibiting the phenomenon of glycation of proteins.

Briefly, the present invention features the administration to an individual subject in need of such treatment, of an effective amount of at least one hydroxystilbene, or composition comprised thereof, to reduce or even inhibit the glycation of proteins, particularly the glycation of proteins of the skin and/or of the structures associated therewith.

This invention thus features a cosmetic/dermatological regime/regimen, comprising administering to an individual subject in need of such treatment, an effective amount of at least one hydroxystilbene, or composition comprised thereof, to reduce or even inhibit the glycation of dermal proteins, for example collagen, and/or the nails, and/or the hair, for example the keratins.

The present invention also features administration of an effective amount of at least one hydroxystilbene, or composition comprised thereof, to preventively and/or curatively treat the signs of aging of the skin or of its associated structures, which are implicated in glycation.

DETAILED DESCRIPTION OF BEST MODE AND SPECIFIC/PREFERRED EMBODIMENTS OF THE INVENTION

More particularly according to the present invention, the preferred hydroxystilbenes are compounds having the structural formula (I):

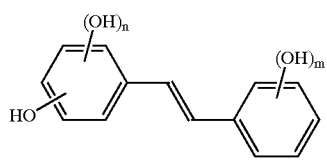

(I)

in which n is an integer ranging from 0 to 4, inclusive and m is an integer ranging from 0 to 5, inclusive. These compounds can be in a cis- or trans-form.

According to the invention, by the term "hydroxystilbene" are intended both the compounds of formula I and the hydroxyalkyl derivatives thereof.

The hydroxystilbenes are compounds that exist in the natural state in plants of the spermatophyte family and particularly in vine. Such compounds, for example such as resveratrol, exist in grapes and in wine.

The hydroxystilbenes are described in the prior art, inter alia, as depigmenting agents, (JP-87/192,040), as vasodilators (EP-96/830,517), as antithrobotic agents (JP-05/016, 413), in the treatment of various cardiovascular afflictions (CA-2,187,990), as inhibitors of mutagenesis and carcinogenesis (JP-06/024,967) or, alternatively, are described as antioxidants.

Among these compounds, resveratrol (or 3,5,4'-trihydroxystilbene) is particularly known for the activities described above principally because it is a natural compound which exists in the skin of grapeseeds and in wine. In this regard, compare the review by Soleas and collaborators (Clinical Biochemistry, vol. 30, No 2, pp. 91–113, 1997) which well summarizes the state of the art regarding this compound and hydroxystilbenes.

However, the ability of the hydroxystilbenes to reduce or even inhibit the phenomenon of glycation was hitherto unknown.

Exemplary hydroxystilbenes according to this invention include the mono-, di-, tri-, tetra-, penta-, hexa-, hepta-, octa- and nonahydroxystilbenes, and the hydroxyalkyl derivatives thereof.

Consistent herewith, the hydroxystilbenes can be administered either alone or as mixtures of any nature and can be of natural or synthetic origin.

Preferred hydroxystilbenes according to the invention include:

4'-hydroxystilbene,
2',4'-dihydroxystilbene,
3',4'-dihydroxystilbene,
4,4'-dihydroxystilbene,
2',4 ',4-trihydroxystilbene,
3,4',4-trihydroxystilbene,
2,4,4',-trihydroxystilbene,
3,4,4'-trihydroxystilbene,
3,4',5-trihydroxystilbene,
2',3,4-trihydroxystilbene,
2,3',4-trihydroxystilbene,
2',2,4'-trihydroxystilbene,
2,4,4'5-tetrahydroxystilbene
2',3,4', 5-tetrahydroxystilbene,
2,2',4,4'-tetrahydroxystilbene,
3,3'2,4'5-tetrahydroxystilbene,
2,3',4,4'-tetrahydroxystilbene,
3,3',4,4'-tetrahydroxystilbene,
3,3',4'5,5'-pentahydroxystilbene,
2,2'4,4',6-pentahydroxystilbene,
2,3'4,4'6-pentahydroxystilbene,
2,2',4,4',6,6'-hexahydroxystilbene.
3,4'5-Trihydroxystilbene, or resveratrol, is more preferred according to the invention.

The hydroxystilbene or composition comprised thereof are particularly well suited according to the invention for topical application onto the skin and/or the nails and/or the hair.

The amount of hydroxystilbene which is administered according to the invention naturally depends upon the desired effect and should be an amount which is effective in reducing or even inhibiting glycation.

For example, the amount of hydroxystilbene which can be used according to the invention advantageously ranges, for example, from 0.001% to 10% and preferably from 0.005% to 5% relative to the total weight of the composition.

In addition, the compositions of the invention are administered for a period of time which is sufficient to elicit the expected effects. To provide an order of magnitude, this duration can be a minimum of 3 weeks, but can also be more than 4 weeks, or even more than 8 weeks.

The subject compositions are especially well suited for cosmetic and dermatological applications, advantageously cosmetic applications.

The compositions of the invention suited for topical application contain a physiologically acceptable medium, i.e., a medium (vehicle, diluent or carrier) which is compatible with the skin, including the scalp, structures associated therewith, mucous membranes and/or the eyes and can constitute, in particular, a cosmetic or dermatological composition.

The subject compositions can be in any pharmaceutical form normally employed in cosmetics and dermatology, and can be, in particular, in the form of an optionally gelled aqueous solution, a dispersion of the lotion type which may contain two phases, an emulsion obtained by dispersing a fatty phase in an aqueous phase (O/W) or conversely (W/O), or a triple emulsion (W/O/W or O/w/O), or a vesicular dispersion of ionic and/or nonionic type. These compositions are prepared according to the usual methods.

The compositions of the invention can be formulated, for example, as a lotion, a gel, an ointment, a cream or a milk, a makeup-removing or cleansing lotion or milk, a shampoo, or a shower gel.

The present invention also features a cosmetic regime/regimen for treating the signs of aging associated with the glycation of proteins, particularly of the skin and/or the nails and/or the hair, comprising topically applying a cosmetic composition containing an effective amount of at least one hydroxystilbene onto the skin and/or the nails and/or the hair, such hydroxystilbene or composition thereof being present in such amounts as to inhibit glycation.

In order to further illustrate the present invention and the advantages thereof, the following specific example is given, it being understood that same is intended only as illustrative and in nowise limitative.

In said example to follow, all parts and percentages are given by weight, unless otherwise indicated.

EXAMPLE

Study of the Effect of Resveratrol on Glycation
Experiment 1

A 1 mg/ml solution of bovine serum albumin dissolved in phosphate-buffered saline (PBS) was incubated at 37° C. for 14 days in the presence or absence of D-ribose at a concentration of 10 $\mu$M or of resveratrol at concentrations of 1 $\mu$M and 10 $\mu$M.

The glycation was evaluated by measuring the fluorescence of the AGEs at $\lambda$em.=440 nm emitted by each sample after excitation at $\lambda$ex.=370 nm.

The inhibition of glycation was visualized by the decrease in fluorescence compared with the sample treated with sugar alone.

The results obtained are reported in Table I below:

TABLE I

|  | 1 $\mu$M resveratrol | 10 $\mu$M resveratrol |
| --- | --- | --- |
| % inhibition | 17% | 29.8% |

Resveratrol exhibited an advantageous anti-glycation effect at and above a concentration of 1 $\mu$M.
Experiment 2:

The anti-glycating power of resveratrol was evaluated on the hair.

The glycation reaction was modelled in vitro in a biochemical model using human hair proteins (keratins) as a support for glycation with ribose.
Protocol:

The test system consisted of isolated hair, incubated in a phosphate buffer (0.2M, pH=7.4) containing 50 mM of ribose (origin: Sigma).

The resveratrol dissolved in water of MilliQ grade was tested at concentrations of $10^{-7}$ M, $10^{-6}$ M, $10^{-5}$ M and $10^{-4}$ M.

The resveratrol was added to the test system containing the isolated hair, the ribose and 10% (V/V) of a 0.5% (w/v) sodium azide solution. The assembly was incubated at 50° C. in the absence of light and air for 14 days.

Control samples, incubated in the presence and absence of ribose, were tested in parallel.

After incubation for 14 days, the incubation media were removed and the hair was washed with a solution containing 10 $\mu$M of guanidium chloride and then in water of MilliQ grade in order to remove all trace of free ribose.

The hair was then placed in a solution containing 50% (v/v) of ethanol and 50 mM of DTT for 15 minutes at 37° C. After washing, the samples were placed in a solution containing 10 mM of 5,5'-dithiobis-2-nitrobenzoic acid.

The absorbance relating to the free cystine residues was measured at 415 nm. The samples were then washed in a 50% (v/v) ethanol solution and then heated for 30 minutes at 100° C. in a 2M hydrazine monohydrate solution (pH 9.4). After addition of a 1 mg/ml solution of phenylhydrazine in a 40% (v/v) acetic acid solution, the samples were incubated for [lacuna] 60° C. and the absorbance relating to the glycated proteins was measured at 390 nm. For each sample, the glycation index was evaluated by the ratio between the absorbance at 390 nm and the absorbance at 415 nm.

$$\% \text{ of inhibition} = \frac{(value_{control+sugar} - value_{product+sugar})}{(value_{control+sugar} - value_{control-sugar})} \times 100$$

The groups of data (control group and treated groups) were processed by means of a variance analysis (ANOVA), followed by a Dunett test.

The results obtained are reported in Table II below:

TABLE II

|  | Control − ribose | Control + ribose | R:$10^{-7}$M | R:$10^{-6}$M | R:$10^{-5}$M | R:$10^{-4}$M |
| --- | --- | --- | --- | --- | --- | --- |
| Glycation index | 0.181 | 1.135 | 0.708* | 0.574* | 0.646* | 0.372* |
| Standard deviation | 0.039 | 0.220 | 0.081 | 0.228 | 0.182 | 0.069 |
| % Inhibition | — | — | 45 | 59 | 51 | 80 |

R: resveratrol; *: $p < 0.05$

Under these experimental conditions, the resveratrol compound exhibited an anti-glycation activity of 80% at a concentration of $10^{-4}$ M.

While the invention has been described in terms of various specific and/or preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime and/or regimen for reducing or inhibiting the glycation of susceptible proteins of the nails and/or the hair of an individual subject in need of such treatment, comprising topically administering to such subject, for such period of time as required to elicit reduction or inhibition of the glycation of the susceptible proteins of the nails and/or the hair, an effective amount of at least one hydroxystilbene compound.

2. A regime and/or regimen for reducing or inhibiting the glycation of the keratins of the nails and/or the hair of an individual subject in need of such treatment, comprising topically administering to such subject, for such period of time as required to elicit reduction or inhibition of the glycation of the keratins of the nails and/or the hair, an effective amount of at least one hydroxystilbene compound.

3. A regime and/or regimen for treating aging of human nails and/or hair by reducing or inhibiting the glycation of susceptible proteins of the nails and/or the hair of an individual subject in need of such treatment, comprising topically administering to such subject, for such period of time as required to elicit reduction or inhibition of the glycation of the susceptible proteins of the nails and/or the hair, an effective amount of at least one hydroxystilbene compound.

4. The regime and/or regimen as defined by claim 1, said at least one hydroxystilbene compound having the structural formula (I):

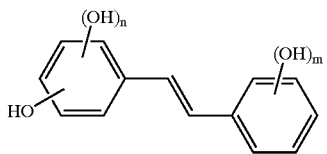

(I)

in which n is an integer ranging from 0 to 4 and m is an integer ranging from 0 to 5.

5. The regime and/or regimen as defined by claim 2, said at least one hydroxystilbene compound having the structural formula (I):

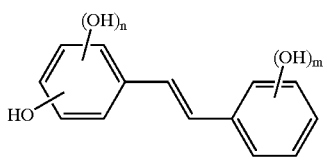

(I)

in which n is an integer ranging from 0 to 4 and m is an integer ranging from 0 to 5.

6. The regime and/or regimen as defined by claim 3, said at least one hydroxystilbene compound having the structural formula (I):

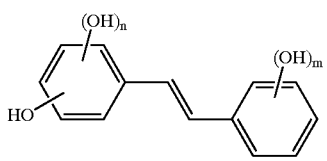

(I)

in which a is an integer ranging from 0 to 4 and m is an integer ranging from 0 to 5.

7. The regime and/or regimen as defied by claim 1, wherein said at least one hydroxystilbene compound is:
4'-hydroxystilbene,
2',4'-dihydroxystilbene,
3',4'-dihydroxystilbene,
4,4'-dihydroxystilbene,
2',4',4-trihydroxystilbene,
3',4',4-trihydroxystilbene,
2,4,4'-trihydroxystilbene,
3,4,4'-trihydroxystilbene,
3,4',5-trihydroxystilbene,
2',3,4-trihydroxystilbene,
2,3',4-trihydroxystilbene,
2',2,4'-trihydroxystilbene,
2,4,4',5-tetrahydroxystilbene,
2',3,4',5-tetrahydroxystilbene,
2,2',4,4'-tetrahydroxystilbene,
3,3',4',4-tetrahydroxystilbene,
2,3 ,4,4'-tetrahydroxystilbene,
3,3',4,4'-tetrahydroxystilbene,
3,3',4',5,5'-pentahydroxystilbene,
2,2',4,4',6-pentahydroxystilbene,
2,3',4,4',6-pentahydroxystilbene,
2',2',4,4',6,6'-hexahydroxystilbene, or combination thereof.

8. The regime and/or regimen as defined by claim 2, wherein said at least one hydroxystilbene compound is:
4'-hydroxystilbene,
2',4'dihydroxystilbene,
3',4'-dihydroxystilbene,
4,4'trihydroxystilbene,
2',4',4-trihydroxystilbene,
3',4',4-trihydroxystilbene,
2,4,4'-trihydroxystilbene,
3,4,4'-trihydroxystilbene,
3,4',5-trihydroxystilbene,
2',3,4-trihydroxystilbene,
2,3',4-trihydroxystilbene,
2',2,4'-trihydroxystilbene,
2,4,4',5-tetrahydroxystilbene,
2',3,4'5-tetrahydroxystilbene,
2,2',4,4'-tetrahydroxystilbene,
3,3',4',5-tetrahydroxystilbene,
2,3',4,4'-tetrahydroxystilbene,
3,3',4,4'-tetrahydroxystilbene,
3,3',4',5,5'-pentahydroxystilbene,
2,2',4,4',6-pentahydroxystilbene,
2,3',4,4',6-pentahydroxystilbene,
2,2',4,4',6,6'-hexahydroxystilbene, or combination thereof.

9. The regime and/or regimen as defined by claim 3, wherein said at least one hydroxystilbene compound is:
4'-hydroxystilbene,
2',4'-dihydroxystilbene,
3',4'dihydroxystilbene,
4,4'dihydroxystilbene,
2',4',4-trihydroxystilbene,
3',4', 4-trihydroxystilbene,
2,4,4'-trihydroxystilbene,
3 ,4,4'-trihydroxystilbene,
3,4', 5-trihydroxystilbene,
2',3,4-trihydroxystilbene,
2,3',4-trihydroxystilbene,
2', 2,4 '-trihydroxystilbene,
2,4,4',5-tetrahydroxystilbene,
2', 3,4', 5-tetrahydroxystilbene,
2,2',4,4'-tetrahydroxystilbene,
3,3',4',5-tetrahydroxystilbene.
2, 3', 4,4'-tetrahydroxystilbene, 3,3', 4,4'-tetrahydroxystilbene, 3,3',4',5.5'-pentahydroxystilbene, 2,2',4,4', 6pentahydroxystilbene, 2,3',4,4', 6-pentahydroxystilbene, 2,2'94,4',6,6'-hexahydroxystilbene, or combination thereof.

10. The regime and/or regimen as defined by claim 7, wherein said at least one hydroxystilbene compound is 3,4',5-trihydroxystilbene.

11. The regime and/or regimen as defined by claim 8, wherein said at least one hydroxystilbene compound is 3,4',5-trihydroxystilbene.

12. The regime and/or regimen as defined by claim 9, wherein said at least one hydroxystilbene compound is 3,4',5-trihydroxystilbene.

13. The regime and/or regimen as defined by claim 1, such period of time as required to elicit the reduction or inhibition of the glycation of the susceptible protiens of the nails and/or the hair being at least three weeks.

14. The regime and/or regimen as defined by claim 2, such period of time as required to elicit the reduction or inhibition of the glycation of the keratins of the nails and/or the hair being at least three weeks.

15. The regime and/or regimen as defined by claim 3, such period of time as required to elicit the reduction or inhibition of the glycation of the susceptible protiens of the nails and/or the lair being at least three weeks.

* * * * *